(12) United States Patent
Soares et al.

(10) Patent No.: US 9,216,275 B2
(45) Date of Patent: Dec. 22, 2015

(54) ADJUSTABLE HEIGHT HYDROCEPHALUS VALVE LOCATION DEVICE

(71) Applicant: DePuy Synthes Products, LLC, Raynham, MA (US)

(72) Inventors: Brian Soares, Norton, MA (US); Alyssa Trigger, South Boston, MA (US); Michael DeFusco, North Attleboro, MA (US); Stephen F. Wilson, North Easton, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 269 days.

(21) Appl. No.: 14/040,865

(22) Filed: Sep. 30, 2013

(65) Prior Publication Data

US 2015/0094643 A1    Apr. 2, 2015

(51) Int. Cl.
*A61M 27/00* (2006.01)
*F16K 31/00* (2006.01)

(52) U.S. Cl.
CPC .............. *A61M 27/006* (2013.01); *F16K 31/00* (2013.01)

(58) Field of Classification Search
CPC .................................................... A61M 27/006
USPC ......................................................... 604/8, 9
See application file for complete search history.

(56) References Cited

U.S. PATENT DOCUMENTS

| | | | |
|---|---|---|---|
| 2,346,773 A | 4/1944 | McBride et al. | |
| 4,156,422 A | 5/1979 | Hildebrandt et al. | |
| 4,540,400 A | 9/1985 | Hooven | |
| 4,551,128 A | 11/1985 | Hakim et al. | |
| 4,595,390 A | 6/1986 | Hakim et al. | |
| 4,608,992 A | 9/1986 | Hakim et al. | |
| 4,615,691 A | 10/1986 | Hakim et al. | |
| 4,676,772 A | 6/1987 | Hooven | |
| 4,772,257 A | 9/1988 | Hakim et al. | |
| 5,146,933 A | 9/1992 | Boyd | |
| 5,236,011 A | 8/1993 | Casada et al. | |
| 5,643,194 A | 7/1997 | Negre | |
| 5,928,182 A | 7/1999 | Kraus et al. | |
| 6,049,989 A | 4/2000 | Lee | |
| 6,094,830 A | 8/2000 | Gloor et al. | |
| 6,840,917 B2 | 1/2005 | Marion | |
| 6,883,241 B2 | 4/2005 | Moskowitz et al. | |
| 6,951,059 B2 | 10/2005 | Moskowitz et al. | |
| 7,921,571 B2 * | 4/2011 | Moureaux et al. | 33/355 R |

(Continued)

FOREIGN PATENT DOCUMENTS

| | | |
|---|---|---|
| EP | 2 236 169 A1 | 10/2010 |
| EP | 2 316 522 A1 | 5/2011 |
| EP | 2 420 284 A2 | 2/2012 |

*Primary Examiner* — Leslie Deak
(74) *Attorney, Agent, or Firm* — Troutman Sanders LLP

(57) ABSTRACT

An adjustable height tool for locating a magnetically readable and settable valve implanted in a living being. The locator can include a wall having a first perimeter. A platform can be disposed within the first perimeter. A valve cut-out can be disposed within the platform and can approximate at least a portion of the shape of the valve. A movable foot can be disposed below the platform by which a displacement element moves the foot at least one of toward or away from the platform. This movement increases or decreases the distance between the platform and the skin/valve. Two or more recesses can be disposed in the foot and the recesses can be aligned with the valve cut-out. The displacement element can maintain the alignment of the recesses and the cut-out while moving the foot.

12 Claims, 9 Drawing Sheets

(56) References Cited

U.S. PATENT DOCUMENTS

| | | |
|---|---|---|
| 8,038,641 B2 | 10/2011 | Soares et al. |
| 8,398,617 B2 | 3/2013 | Ginggen et al. |
| 2002/0022793 A1 | 2/2002 | Bertrand et al. |
| 2005/0022403 A1 | 2/2005 | Moskowitz et al. |
| 2006/0009780 A1 | 1/2006 | Foley et al. |
| 2010/0249690 A1* | 9/2010 | Soares et al. ............... 604/9 |
| 2011/0048539 A1 | 3/2011 | Negre et al. |
| 2011/0105991 A1 | 5/2011 | Roth et al. |
| 2011/0105992 A1 | 5/2011 | Girardin et al. |
| 2011/0105993 A1 | 5/2011 | Girardin et al. |
| 2011/0105994 A1 | 5/2011 | Ginggen et al. |
| 2012/0046595 A1 | 2/2012 | Wilson et al. |
| 2013/0102951 A1 | 4/2013 | Swoboda et al. |

* cited by examiner

Fig. 1A
Fig. 1B
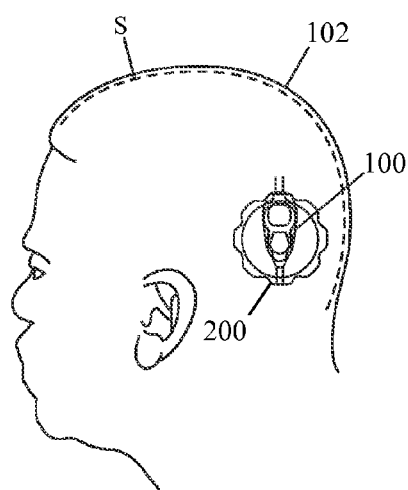
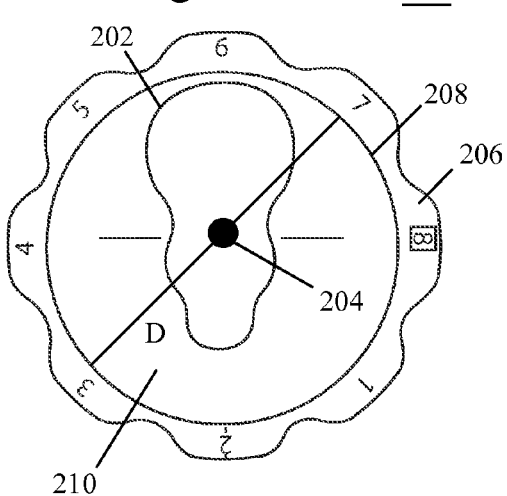
Fig. 1C

ADJUSTABLE HEIGHT HYDROCEPHALUS VALVE LOCATION DEVICE

FIELD OF THE INVENTION

The invention relates generally to surgically implantable fluid drainage systems. More specifically, the invention relates to extracorporeal tools for locating adjustable valves used for cerebrospinal fluid drainage.

BACKGROUND

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the bloodstream. Typically, the shunt valve is palpatable by the physician through the patient's skin after implantation. The shunt valves, which can have a variety of configurations, can be designed to allow adjustment of their fluid drainage characteristics after implantation.

It is also important to be able to externally read or verify the setting of the valve. With some adjustable valves, x-ray images are used to determine the current setting of the valve, before and after adjustment. With other adjustable valves, the orientation of a rotor in the valve can be read magnetically, using a magnetic compass-like device positioned above the valve, outside the skin of the patient. In examples, both the adjuster and the indicator are used in conjunction with a locator. The locator tool is used in the process of determining the location of the valve under the skin and subsequently to maintain this established position. The adjuster and the indicator tools engage within the locator tool to perform their function.

Although tools and methods exist for adjusting CSF shunt valve settings, as do other tools and methods for reading a valve setting, some have difficulty performing their function if the underlying valve protrudes too far from the skull into the locator. These are instances where the patient may have a thick or thin scalp, or a smaller or larger skull than is typical. In these instances, the valve interferes with the placement and operation of the adjustor and/or indicator. Parallel placement of the locator to the implanted valve while in closest proximity to the implanted valve whilst permitting complete engagement between the locator and the indicator and adjustment tools enables successful operation of these tools.

Thus, a need exists for a locator that can adjust for the height of the valve to enable the locator to be held by the user against the skin in a position generally parallel to the implanted valve so as to prevent interference between the skin/valve and the adjuster/locator or the skin/valve and the indicator/locator.

SUMMARY

Accordingly, the present invention provides an adjustable height tool for determining the location of and subsequently to maintaining this established position of a magnetically readable and settable valve implanted in a living being. The locator can include a wall having a first perimeter. This perimeter can be a function of a diameter and/or circumference of the wall. A platform can be disposed within the first perimeter, typically near the center or bottom of the wall. A valve cut-out can be disposed within the platform. The cut-out approximates at least a portion of the shape of the valve, and can receive that portion or the skin thereabove. A movable foot can be disposed below the platform by which a displacement element moves the foot, at least one of, toward or away from the platform. This movement increases or decreases the distance between the platform and the skin/valve. Two or more recesses can be disposed in the foot and the recesses can be aligned with the valve cut-out. This alignment can allow any portion of the valve not captured inside the space of the wall or foot to have clearance under the foot. Additionally, the displacement element maintains the alignment of the recesses and the cut-out while moving the foot to minimize clearance or interference between the platform and the skin/valve.

The above tool can also include a plurality of indicators disposed on the wall. These can indicate one or more valve settings. The plurality of indicators can have a fixed orientation in relation to the cut-out. Then, the displacement element can maintain the orientation of the plurality of indicators and the cut-out while moving the foot. This can allow for consistent readings and adjustments of the valve.

Turning to the displacement element, it can, in one example, only permit movement of the foot in fixed increments. Alternately, it can be infinitely adjustable within a range of heights between the platform and the skin/valve or bottom of the foot. In addition, the displacement element can provide feedback as to the movement of the foot.

Another example of a locator can include the wall having the first perimeter, the platform disposed within the first perimeter and the valve cut-out disposed within the platform. In this example, the cut-out receives a portion of the valve and the displacement element moves the foot to control the amount of the valve received in the valve cut-out. As above, the movable foot can be disposed below the platform. In other examples, at least a portion of the foot can be disposed above the platform and displace below the platform as the foot is extended.

As above, the locator can also have two or more recesses disposed in the foot and aligned with the valve cut-out. Further, the displacement element can maintain the alignment of the recesses and the cut-out while moving the foot. Further-more, the plurality of indicators can be disposed on the wall indicating one or more valve settings. These plurality of indicators have a fixed orientation in relation to the cut-out and the displacement element can maintain the orientation of the plurality of indicators and the cut-out while moving the foot.

Another example is a method for locating the magnetically readable and settable valve implanted in a living being using the adjustable height tool. The steps can include locating the valve, positioning the locator over the valve, adjusting the height of the foot of the locator so that the foot of the locator supports the hand placement of the locator while the platform is in closest proximity to the valve. Note that too much offset between the locator and the indicator/adjustor generally results in the magnetic coupling between the particular tool and valve that is less than optimal, making it more difficult to read or adjust the valve with certainty. The closer the tool is to the implant the better the ability to read or adjust the valve. When the tool is too close to the implant, it means either, or, both of the below examples. In one example, the skin/valve protrudes thru the cutout and the locator sits in contact with the skin above the valve and then tilts to contact some portion of the foot. This is an unstable position and anything less than parallel orientation between the valve and tools is less than ideal. Another example is that the skin protruding thru cutout prevents the indicator and the adjustor from sitting flush within the locator, and again this would be less than parallel, and thus less than ideal. However, once properly placed, the valve can be adjusted. Other steps can be orienting the cut-out of the locator with the valve and adjusting the height of the foot of the locator while maintaining the orientation of the cut-out and valve.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

FIG. 1A is an illustration of a typical valve implanted in a patient;

FIG. 1B is a top view of an example of a locator;

FIG. 1C is an illustration of the valve and locator as used on a patient;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Methods and integrated tools of the present invention enable a physician to consistently and reliably locate an implantable, magnetically settable valve (valve) and change a setting of (adjust) the valve from a current setting to a target setting without interference from the valve. In an example, the valve is used to control, via its setting, at least one of CSF drainage flow and pressure for a patient with hydrocephalus, is implanted under a patient's scalp or another portion of the patient's skin, and is adjustable from outside (above) the patient's skin but needs to be located.

Other tools and methods for extracorporeally reading and adjusting a hydrocephalus valve are disclosed in U.S. Pat. No. 8,038,641 entitled "Tools and Methods for Programming an Implantable Valve", which is hereby incorporated by reference in its entirety. Within the scope of the present invention, features of the various examples disclosed herein can be used in any combination to construct additional integrated tools and methods for reading and adjusting an implantable valve.

Figure 2A:
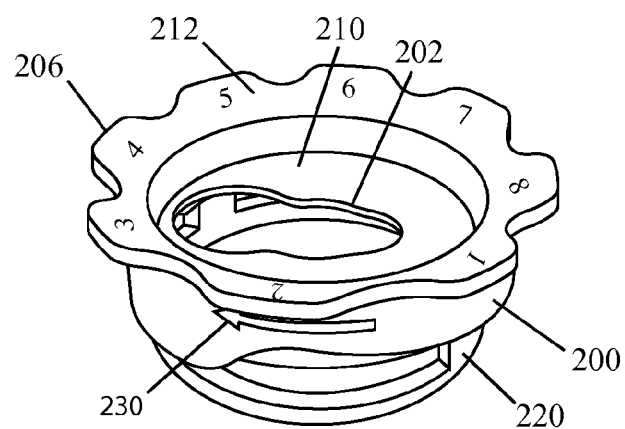
FIG. 2A is a top-side profile view of an example of a locator.
Figure 2B:
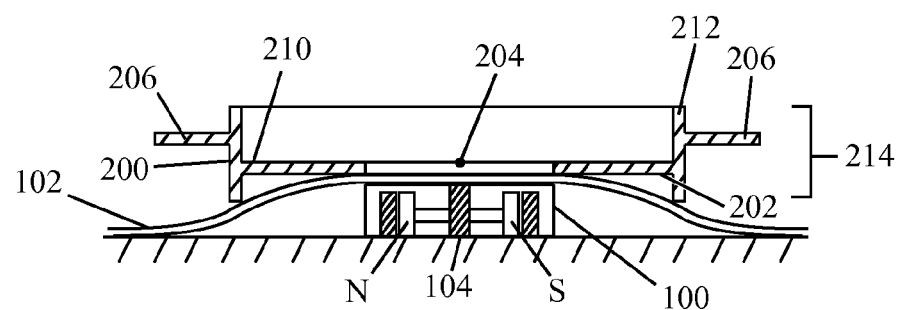
FIG. 2B is a cross-sectional view along line II-II of FIG. 1C illustrating the valve and locator in use with the foot retracted.
Figure 2C:
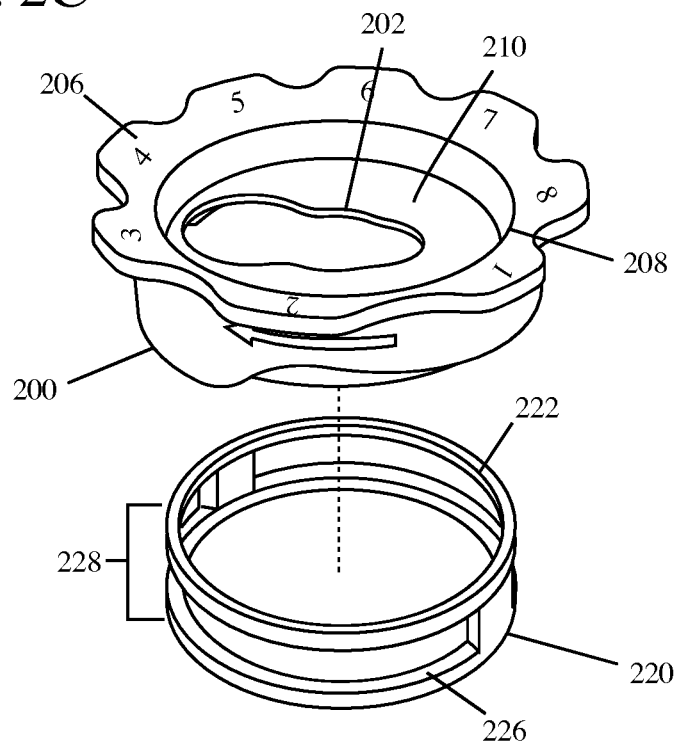
FIG. 2C is an exploded view of the locator.
Figure 3:
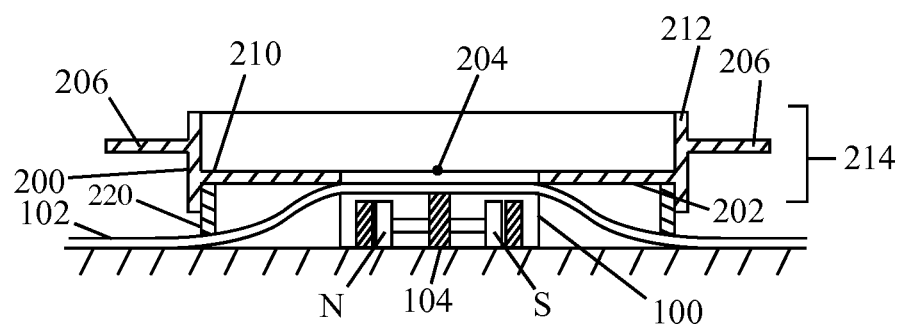
FIG. 3 is a cross-sectional view along line II-II of FIG. 1C illustrating the valve and locator in use with the foot extended.

FIGS. 1A, 2B, and 3 illustrate a generalized implantable valve 100 implanted beneath a patient's skin 102. The valve 100 includes a magnetic axis 104 which is the point of reference used to adjust the valve 100 or determine its settings. In an example, the valve 100 has a plurality of predetermined settings corresponding to a plurality of predetermined flows and pressures. In an example, the plurality of settings comprises eight settings.

It is to be understood that the valve 100 can be any magnetically settable, implantable valve. In an embodiment, the valve 100 is unlocked by placing a magnetic field over the magnetic axis 104. In a further embodiment, the attractive magnetic field for setting the valve can be provided by a single magnetic source that can be either a permanent magnet or an electromagnet.

FIG. 1A illustrates the valve 100 implanted under the skin 102 of a patient's skull S. Once implanted, the valve is under the skin and typically covered by hair. Additionally, the area surrounding the valve may experience localized swelling, especially after surgery. Also, as mentioned above, the patient may have a thin/thick scalp or small/large skull. Thus, a fixed foot can accommodate a range of sizes, while an adjustable foot accommodates a larger range, of bigger or smaller sizes. To locate the valve 100 under the skin 102, the user typically palpates the skin 102 until she can feel the valve 100. To facilitate the adjustment of the valve, a locator 200 is placed over the valve 100 on top of the skin 102 of the skull S.

FIG. 1B illustrates an example of the locator 200. The locator 200 can be typically circular and can have a diameter D. The locator 200 can have a cut-out 202 or gap shaped similar to the valve 100. The presence of the cut-out 202 allows the user to palpate, to feel and reposition the locator 200. Further, where skin is not thick or swollen, the cut-out 202 in the shape of the valve 100 can aid in positioning and orienting by mating the bulge under the skin with the cut-out 202. This allows the locator 200 to be oriented in the proper direction when placed over the valve 100. The cut-out 202 can be oriented such that once placed over the valve 100 the magnetic axis 104 is aligned with a center 204 of the locator 200. While an example can be circular, the locator 200 can have any shape to allow an adjustor and/or indicator to perform their functions. Thus, in one example, the locator 200 can be non-circular and composed of numerous line segments.

The locator 200 can also have indicators 206, these can be visual markings without or with petals or tabs extending outside a first perimeter 208 defined by the diameter D (wherein first perimeter 208 can equal π×diameter D). FIG. 1C illustrates a top view of the locator 200 placed over the valve 100 on the patient's skull S.

Turning now to FIGS. 2A and 2B, a top-side and cross section of the locator 200 are illustrated, respectively. The cut-out 202 of the locator 200 can be placed over the valve 100 and can even receive a small portion of the valve 100, as the skin 102 may allow. The cut-out 202 can be formed in a platform 210 of the locator 200. The locator 200 also can have a circumferential wall 212 depending from, and past, the platform 210 and, in one example, encircling the entire platform 210. The indicators 206 can depend from the circumferential wall 212 and a height 214 of the circumferential wall 212 can form a space or volume, within the locator 200. This space can be both above and below the platform 210.

In the normal operation of the locator 200, as noted above, it is placed over the valve 100. The valve 100 and skin 102 can stay below the platform 210 and may not protrude through the cut-out 202. When an adjustor (not illustrated) is placed within the locator 200, it functions best if it is in contact with the platform 210 while positioned as close to the implanted valve as allowable and while parallel to the valve. In that way, the valve can be adjusted. However, if the skin 102 does protrude too much through the cut-out 202 such that the indicator or adjustor do not sit flush or the locator sits against the skin in a position less than parallel to the valve, the present example of the locator 200 can include an adjustable foot 220 below the platform 210 to increase the distance between the valve 102 and the cut-out 202/platform 210. See, FIGS. 2A, 2C, 3, and 4.

The foot 220 engages the patient's skin 102 and can be displaced both toward and away from the platform 210 to remove or create additional space below the locator 200. The foot 220 has a second perimeter 222 approximately equal to the first perimeter 208 of the wall 212. The foot 220 can be disposed within or outside of the first perimeter 208 of the wall 212, thus dictating its size in relation to the first perimeter 208.

The foot 220 can have recesses 224 formed in at least two places along the perimeter 222. The recesses 224 are aligned with the cut-out 202 and allow a portion of the valve 100 to pass under the foot 220 when the locator 200 is placed over the valve 100.

The foot 220 is moved in relation to the platform 210 with a displacement element 226. The displacement element 226 can be one or more of the many examples noted below, but all have a common feature. The displacement element 226 can keep the recesses 224 aligned with the cut-out 202 when the foot 220 is being displaced. Examples of the displacement element 226 can be sloped groove and pin relationship, spaced threads, detents, loading by an elastic element, rotating cuff, etc.

The adjustment element 226 can displace the foot 220 over a range of additional heights 228. The additional height 228 can be dynamic, in which the foot 220 can be at any height within the range of additional heights 228. Alternately, the additional heights 228 can be stepwise, in which the heights 228 change in a fixed sequence of set increments. These heights 228 can also control the amount, if any, of the valve 100 and/or skin 102 that protrudes through the cut-out 202.

For example, the full additional height 228 can be 7.5 mm. Using a spring as the adjustment element 226, the platform 210 can be at full height above the skin 102 and the locator 200 depressed during use. This allows the cut-out 202 to be moved into contact with the valve 100 without regard of the exact distance the valve 100 protrudes from the skin 102. Alternately, the additional height 228 can be incremented in equal 1.5 mm "steps." Differently, each step can have a distinct height. For example, the five steps can be 0.5 mm, 0.75 mm, 1.0 mm, 1.5 mm, 1.75 mm, and 2.0 mm. The locator 200 can also include a marker 230 to assist the user as to which direction to actuate either the foot 220 or the adjustment element 226 to increase the height 228. Alternately, the marker 230 can indicate the direction to decrease the height 228.

In an example, the height can be adjusted by pulling or turning the foot 220 in relation to the wall 212 to increase or decrease the distance. Each step can be accompanied by an audio or tactile indication to inform a user as to that the platform 210 has changed height through the "step." The indications can be a "click" as the foot 220 changes increments, or some form of vibration. Further, the foot 220 can be locked into place by common means, either temporarily or permanently, once the proper height is determined.

Another example of the foot 220 and adjustment element 226 is that one or both of them keep the recesses 224 aligned with the indicators 206. This can be important, as the indicators 206 should always stay is the same relation to the cut-out 202 for consistency in the readings and adjustment of the valve 100. For example, as illustrated in FIG. 1B, the number "6" is at the 12 o'clock position when the cut-out has the illustrated "vertical" orientation, and that indicator should remain consistently located as the foot 220 is displaced.

FIG. 3 illustrates the cross-section of the locator 200 while engaged with the patient's skin 102 over the valve 100. As compared with FIG. 2B, the foot 220 provides additional clearance between the platform 210 and the skin 102, so the skin can be swollen into that space.

Figure 4:
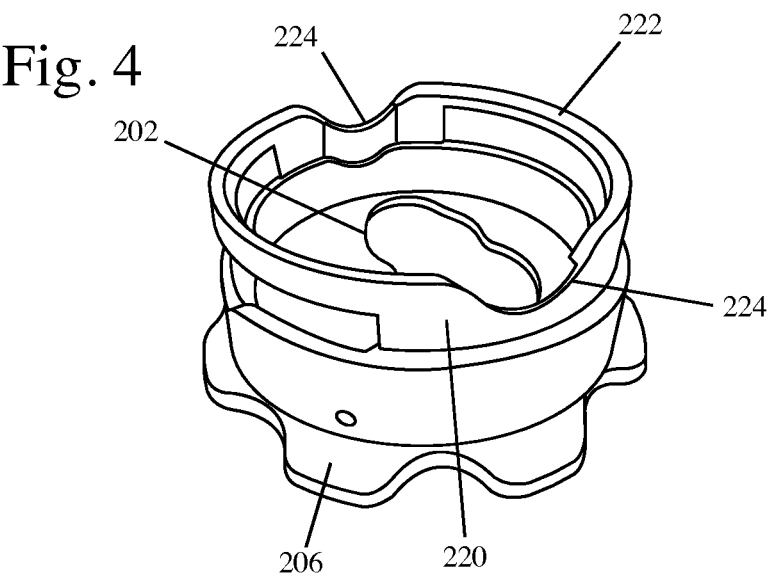
FIG. 4 is a bottom-side profile view of an example of a locator.
Figure 5:
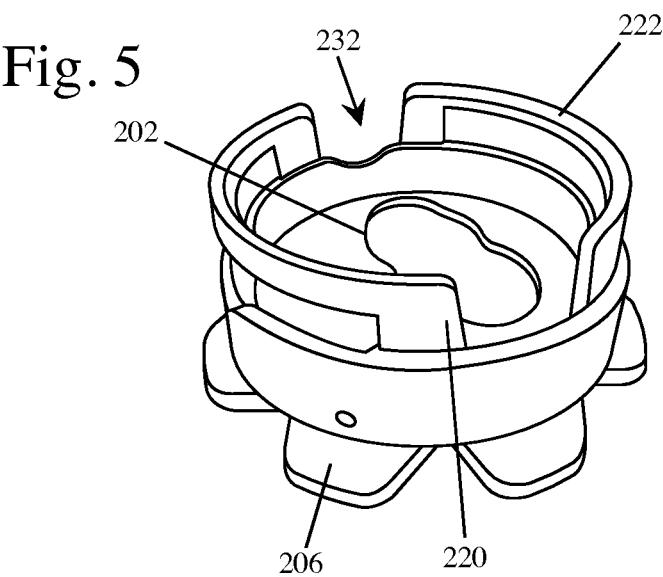
FIG. 5 is a bottom-side profile view of another example of a locator.

FIG. 4 illustrates the bottom of the locator 200 and the alignment of the recesses 224 and the cut-out 202. FIG. 5 illustrates another example, illustrated from the bottom. While the above examples describe a foot 220, the foot 220 can also include two or more feet. The foot 220 illustrated in FIG. 5, for example, can be two unconnected arcs. In a multiple foot 220 example, the recesses 224 can be gaps 232 between the feet 220 or still formed in the feet.

Figure 6:
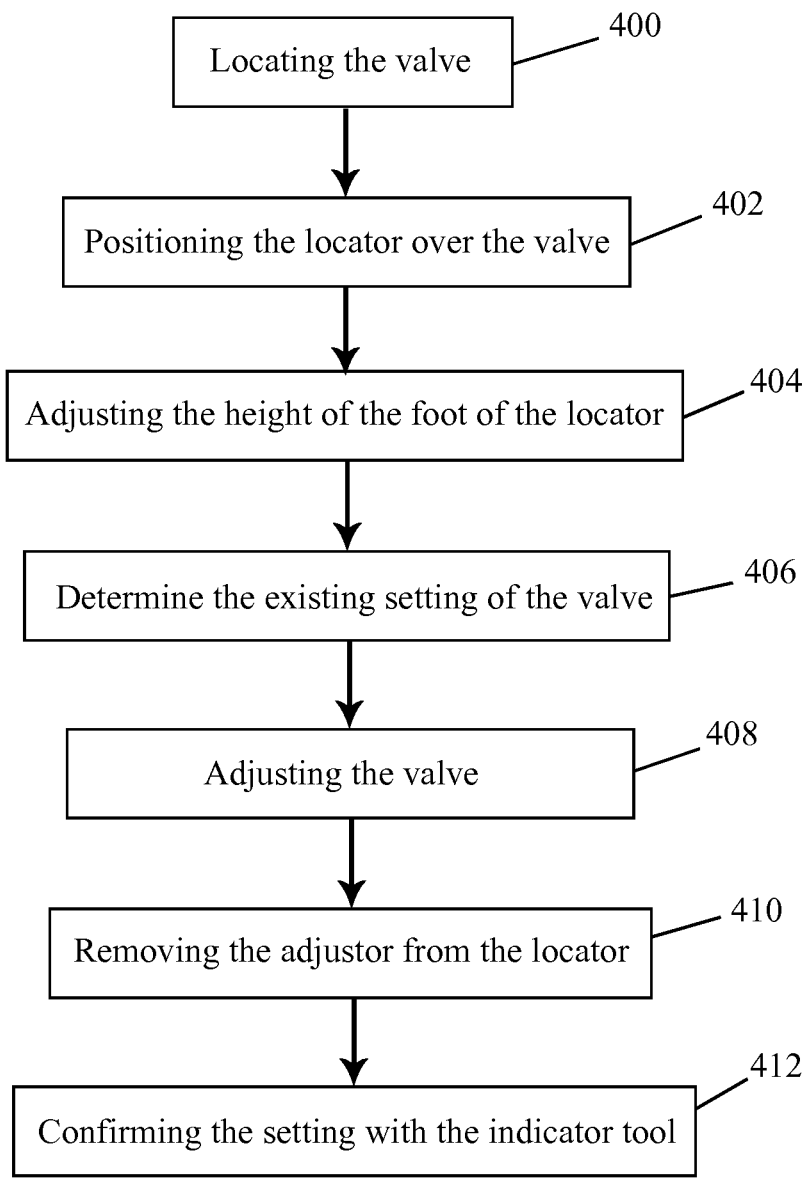
FIG. 6 is flow chart illustrating an example of a method of adjusting the locator.

FIG. 6 illustrates a flow chart of an example of a method using the above device. A user can palpate the skin 102 to locate the valve 100 (step 400). The user can position the locator 200 over the valve 100 once located (step 402). The user can then adjust the height of the foot 220 of the locator 200 (step 404) so the valve 100 and/or skin 102 does not protrude through the cut-out 202. In use, avoiding contact between skin/valve and cut-out 202 means that the foot 220 supports the locator 200 on the skin 102 and the locator 200 can then be parallel to the implanted valve 100.

Further, with the locator 200 in place, the user can determine the existing setting of the valve 100, with, for example, an indicator tool (not illustrated) (step 406). The user then inserts the adjustor 300 in the locator 200 to adjust the valve 100 (step 408), in one example, by rotating the adjustor 300. The adjustor 300 is then removed from the locator 200 (step 410) and the new setting can be confirmed with the indicator tool (step 412).

Figure 7:
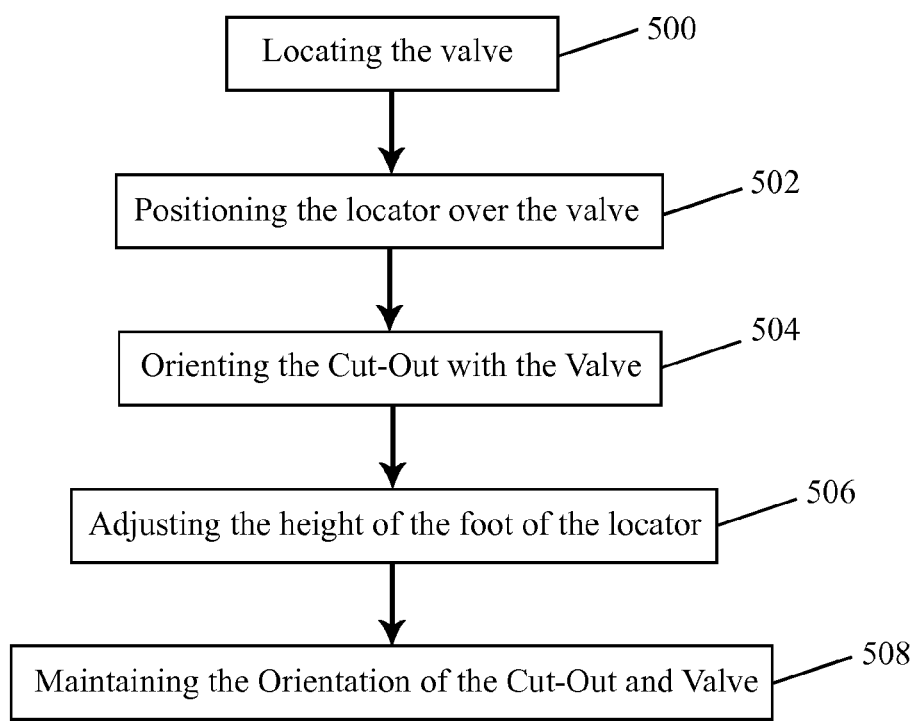
FIG. 7 is flow chart illustrating another example of a method of adjusting the locator.

FIG. 7 illustrates another method of the present invention. As above, the valve 100 is located (step 500). The locator 200 is placed over the valve 100 (step 502). The locator 200 is oriented as to align the cut-out 202 with the valve 100 (step 504). The foot 220 is then adjusted to increase the height of the platform 210 above the skin 102 of the patient (step 506) to achieve minimal contact and parallel positioning. While the foot 220 is adjusted, the orientation of the locator 200 is relation to the valve 100 is maintained (step 508). The method can also include the steps to determine and adjust the settings of the valve 100 as described above.

Figure 8:
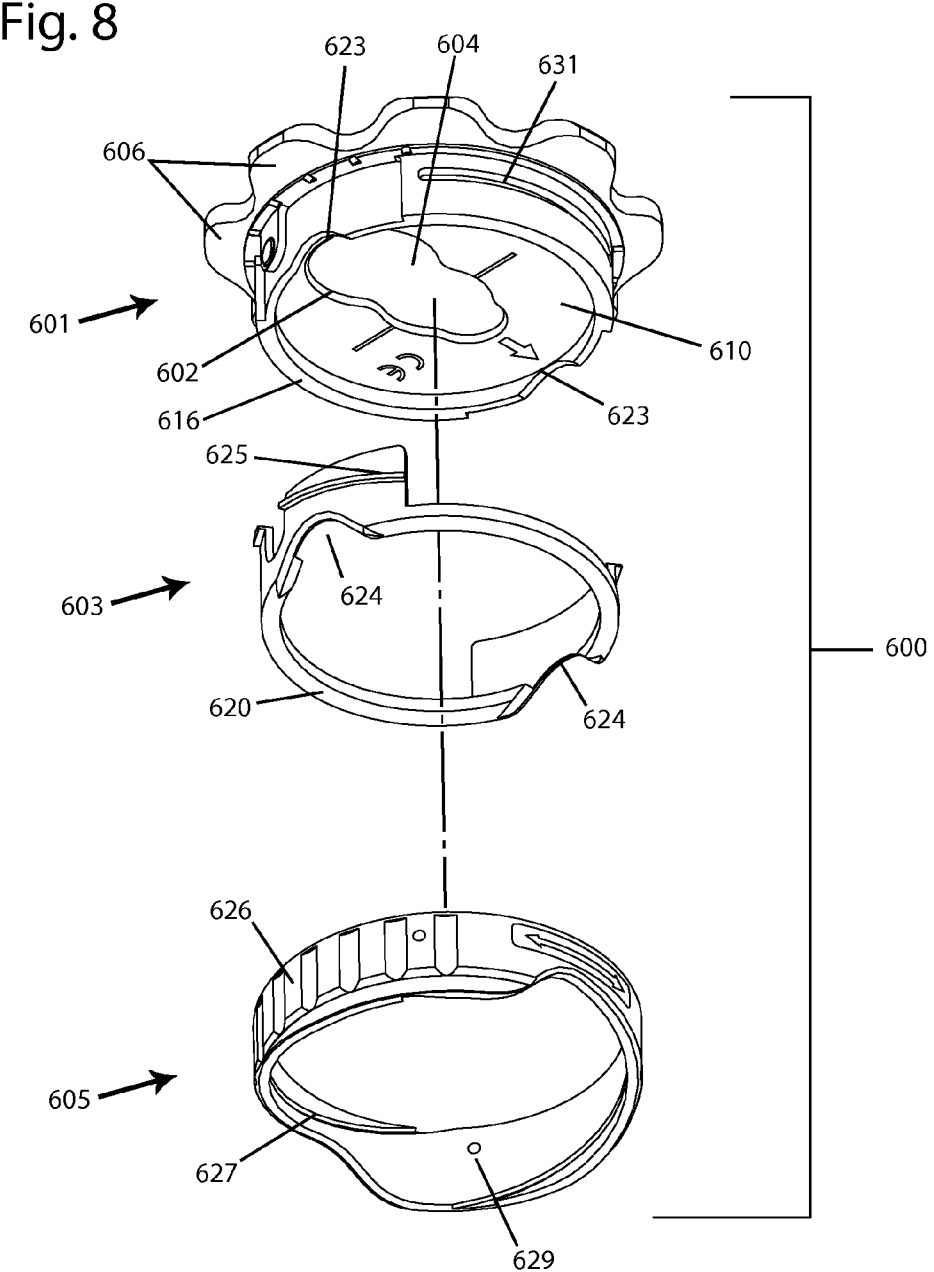
FIG. 8 is an exploded view of a further example of a locator.
Figure 9:
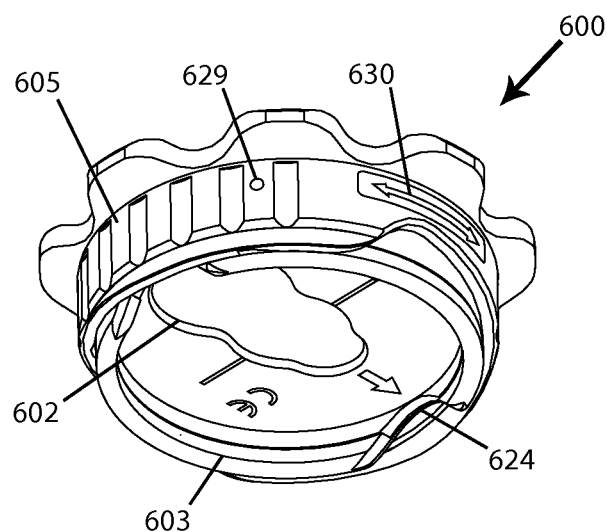
FIG. 9 is a bottom-side profile view of a further example of a locator.
Figure 10:
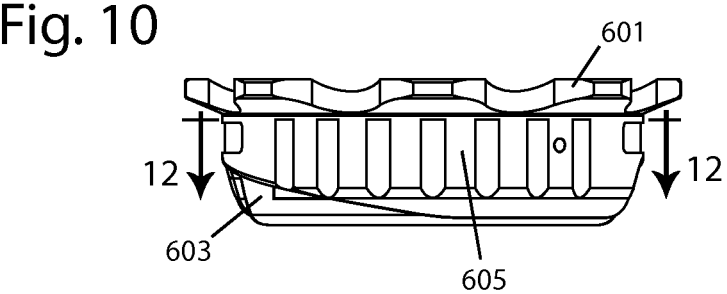
FIGS. 10 and 10A are side views of the further example of the locator in the retracted and extended positions, respectively.
Figure 10A:
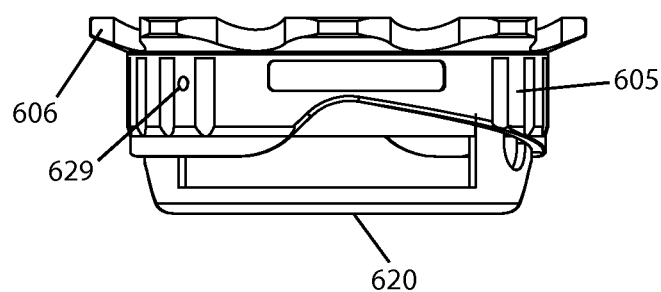
Figure 11:
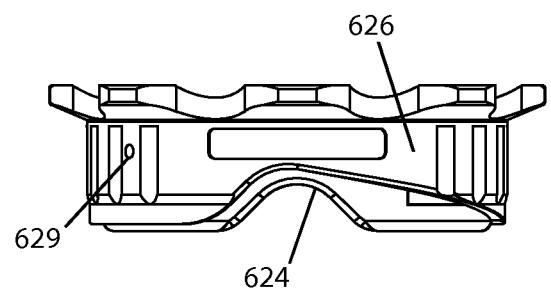
FIGS. 11 and 11A are front side views of the further example of the locator in the retracted and extended positions, respectively.
Figure 11A:
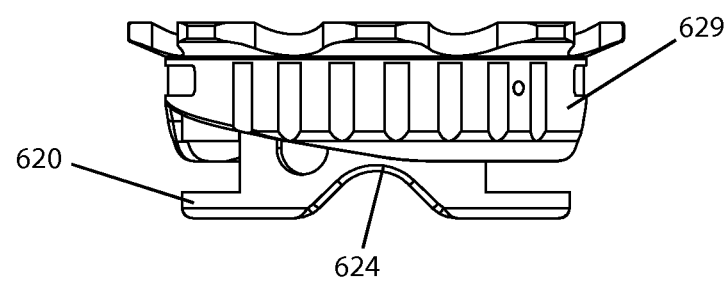
Figure 12:
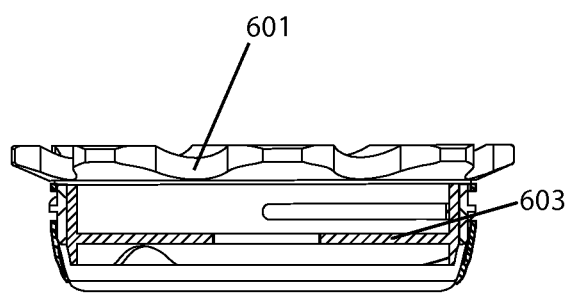
FIG. 12 is a cross-sectional view along line 12-12 of FIG. 10A.

FIGS. 8-12 illustrate a further example of the locator 600. The locator 600 can be divided into three parts, a crown 601, a frame 603, and an adjustment ring 605. FIG. 8 illustrates all three parts separated. The crown 601 can have a cut-out 602 or a gap shaped similar to the valve 100. The cut-out 602 can be oriented such that once placed over the valve 100 the magnetic axis 104 is aligned with a center 604 of the locator 600. The cut-out 606 can be formed in a platform 610 on the crown 601. The crown 601 also can have a circumferential wall 616 depending from, and past, the platform 610 and, in one example, encircling the entire platform 610. Indicators 606, which can be visual markings denoting the setting of the valve 100, can depend from the circumferential wall 616. The circumferential wall 616 can also form a space or volume, within the crown 601. This space can be both above and below the platform 610. In one example, the crown 601 can also include minor recesses 623 aligned with the cut-out 602 and the recesses 624 in the foot 620.

Turning to the example of the frame 603, it can generally include an adjustable foot 620 below the platform 610 to increase the distance between the valve 106 and the cut-out 602/platform 610. The foot 660 can be displaced both toward and away from the platform 610 to remove or create additional space below the locator 600. The foot 620 can include the recesses 624 formed in at least two places along the frame 603. The recesses 624 can be aligned with the cut-out 602 and allow a portion of the valve 100 to pass under the foot 620 when the locator 600 is placed over the valve 100.

The frame 603 can also include a male thread 625 that mates with a female thread 627 on the adjustment ring 205. Note that the threads can be reversed in different examples. The adjustment ring 605 can act as part of the displacement element 626. The combination of the male thread 625 and the female thread 627 can move the foot 620/frame 603 in or out relative to the crown 601. An interference element 629 between the adjustment ring 605 and the crown 601 maintains the orientation of the two pieces to each other. The interference element 629 can be pins which can move in a circumferential groove 631 formed in the crown 601. The crown 601 can also include can also include an indicator 630, illustrated as an arrow, to inform the user of the proper direction to twist the adjustment ring 205 to displace the foot 620. The interference element 629 can, in some examples, allow for the smooth displacement of the foot 620 when the adjustment ring 605 is turned. In other examples, the interference element 629 can permit only a step-wise height change by the foot 620. The changes in height can either be uniform, or varied, as noted above.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. An adjustable height tool for locating a readable and settable valve implanted in a living being, the locator comprising:
   a wall having a first perimeter;
   a platform disposed within the first perimeter;
   a valve cut-out disposed within the platform;
   a movable foot disposed below the platform;
   a displacement element configured to move the foot at least one of toward or away from the platform upon rotation of the displacement element; and
   two or more recesses disposed in the foot and aligned with the valve cut-out;
   wherein the displacement element maintains the alignment of the recesses and the cut-out while moving the foot.

2. The tool of claim 1, wherein the locator further comprises:
   a plurality of indicators disposed on the wall indicating one or more valve settings;
   wherein the plurality of indicators have a fixed orientation in relation to the cut-out; and
   wherein the displacement element maintains the orientation of the plurality of indicators and the cut-out while moving the foot.

3. The tool of claim 1, wherein the displacement element only permits movement of the foot in fixed increments.

4. The tool of claim 1, wherein the displacement element provides feedback as to the movement of the foot.

5. The tool of claim 1, wherein the foot comprises two or more feet.

6. The tool of claim 1, wherein the foot comprises two or more feet and the recesses are formed from gaps between the feet.

7. An adjustable height tool for locating a readable and settable valve implanted in a living being, the locator comprising:
   a wall having a first perimeter;
   a platform disposed within the first perimeter;
   a valve cut-out disposed within the platform and receiving a portion of the valve;
   a movable foot disposed below the platform; and
   a displacement element configured to move the foot at least one of toward or away from the platform upon rotation of the displacement element, thereby controlling the amount of the valve received in the valve cut-out.

8. The tool of claim 7, wherein the locator further comprises:
   two or more recesses disposed in the foot and aligned with the valve cut-out;
   wherein the displacement element maintains the alignment of the recesses and the cut-out while moving the foot.

9. The tool of claim 7, wherein the locator further comprises:

a plurality of indicators disposed on the wall indicating one or more valve settings;
wherein the plurality of indicators have a fixed orientation in relation to the cut-out; and
wherein the displacement element maintains the orientation of the plurality of indicators and the cut-out while moving the foot.

10. The tool of claim 7, wherein:
the wall, the platform and the valve cut-out are disposed in a crown;
the foot is disposed on a frame and comprises two or more recesses; and
the displacement element is disposed on an adjustment ring,
wherein the frame and the adjustment ring comprise mating threads,
wherein the crown and the adjustment ring are engaged by an interference element,
wherein, when the adjustment ring is rotated, the frame is displaced relative to the crown and the interference element maintains an alignment of the recesses and the cut-out.

11. A method for locating a magnetically readable and settable valve implanted in a living being using an adjustable height tool, the steps comprising:
locating the valve;
positioning a locator over the valve; wherein the locator comprises a wall having a first perimeter, a platform disposed within the first perimeter, a valve cut-out disposed within the platform, a movable foot disposed below the platform, a displacement element configured to move the foot at least one of toward or away from the platform upon rotation of the displacement element, and two or more recesses disposed in the foot and aligned with the valve cut-out;
adjusting the height of a foot of the locator by rotating the displacement element; and
adjusting the valve with an adjustor.

12. The method of claim 11, further comprising the steps of:
orienting a cut-out of the locator with the valve;
wherein, when adjusting the height of the foot of the locator, maintaining the orientation of the cut-out and valve.

* * * * *